United States Patent [19]

Kolc et al.

[11] Patent Number: 4,528,020

[45] Date of Patent: Jul. 9, 1985

[54] UREASE INHIBITED UREA BASED FERTILIZER COMPOSITIONS

[75] Inventors: Jaroslav F. Kolc, Randolph; Michael D. Swerdloff, Parsippany; Milorad M. Rogic, Whippany, all of N.J.; Larry L. Hendrickson, Camillus, N.Y.

[73] Assignee: Allied Corporation, Morris Township, Morris County, N.J.

[21] Appl. No.: 505,016

[22] Filed: Jun. 16, 1983

[51] Int. Cl.$^3$ .............................................. C05C 9/00
[52] U.S. Cl. .......................................... 71/28; 71/902
[58] Field of Search ............................ 71/11, 27–30, 71/902

[56] References Cited

U.S. PATENT DOCUMENTS

| 4,083,996 | 4/1978 | Tanaka et al. | 424/315 |
| 4,157,396 | 1/1979 | Tanaka et al. | 424/266 |
| 4,182,881 | 1/1980 | Bayless et al. | 546/22 |
| 4,222,948 | 9/1980 | Alaimo et al. | 260/397.7 R |
| 4,225,526 | 9/1980 | Alaimo et al. | 260/397.7 R |
| 4,242,325 | 12/1980 | Bayless et al. | 424/218 |

FOREIGN PATENT DOCUMENTS 1094802 12/1967 United Kingdom .
1494774 12/1977 United Kingdom .

OTHER PUBLICATIONS

1978, CA, vol. 89, Abst. #89: 89455k, Matzel et al.
1979, CA, vol. 90, Abst. #90: 21340j, Oertal et al.
1979, CA, vol. 91, Abst. #91: 122724p, Matzel et al.
1979, CA, vol. 91, Abst. #91: 139619f, Heber et al.
1981, CA, vol. 94, Abst. #94: 101951g, Vlek et al.
1981, CA, vol. 94, Abst. #94: 139429f, Bayless et al.

Primary Examiner—Ferris H. Lander
Attorney, Agent, or Firm—Richard C. Stewart, II

[57] ABSTRACT

The invention relates to novel urease inhibited fertilizer compositions containing urea and a urease inhibiting amount of hydroxamic acid or diaminophosphinyl compounds, and methods and composition for inhibiting the activity of urease through use of such compounds.

27 Claims, No Drawings

UREASE INHIBITED UREA BASED FERTILIZER COMPOSITIONS

BACKGROUND OF THE INVENTION

1. Field of the Invention

This invention relates to urease inhibited urea based fertilizer compositions. More particularly, this invention relates to urease inhibited urea based fertilizer compositions which contain certain diaminophosphinyl or hydroxamic acid compounds as the urease inhibitors, and to methods and compositions for inhibiting the action of soil urease through use of such compounds.

2. The Prior Art

It is well known in the art to use urea and urea compositions in fertilizers, for application to the soil. The effective life of such fertilizers, however, is of short duration wherever microbiological activity exists in the soil to which the fertilizer is applied. This is due to the fact that urea is hydrolyzed rapidly, and nitrogen is lost in the form of ammonia, when urea is placed under or on the surface of soil which contains urease. Urease, a crystallizable enzyme occurring in numerous bacteria and fungi, as for example *Micrococcus urease,* catalyzes the conversion of urea into ammonia and carbon dioxide. The reactions are as follows:

$$CO(NH_2)_2 + 2H_2O \xrightarrow{Urease} 2NH_3 + H_2CO_3$$

$$NH_3 + H_2O \longrightarrow NH_4^+ + OH^-$$

A portion of the ammonia thus formed is held by absorbing constituents of the soil and is available to plants as nutrient. However, a large amount of the ammonia may be lost to the air. A further problem resulting from the action of urease is the accumulation of ammonium in the soil which can damage germinating seedlings and young plants.

One approach to the reduction of problems resulting from the activity of soil urease toward soil applied urea is to find compounds that inhibit urease activity when applied to soils in conjunction with fertilizer urea. This approach has received considerable attention, and several classes of compounds have been used as urease inhibitors.

For example, certain prior art describes various phosphoro compounds which are useful as urease inhibitors. Illustrative of such prior art are East German Pat. Nos. 142,714; 212,026; 122,177; 122,621 and 130,936, and Great Britain Pat. No. 1,494,774 which describe various phosphorodiamidate compounds as urease inhibitors. Also exemplary of such prior art is U.S. Pat. No. 4,242,325 which describes a method of controlling the enzymatic decomposition of urea to ammonia and carbonic acid due to the action of urease which comprises exposing the enzyme to certain phosphoric triamide compounds. U.S. Pat. No. 4,182,881 describes the use of certain N-[diaminophosphinyl]arylcarboxyamide compounds as inhibitors of the enzyme urease in the urinary tract. U.S. Pat. No. 4,225,526 describes the use of 8-[(4-aminophenyl)sulfonyl]amino-2-naphthalenyl phosphorodiamidate compounds as inhibitors of the enzyme urease, and U.S. Pat. No. 4,222,948 describes the use of ([(4-aminophenyl)sulfonyl]amino)phenyl phosphorodiamidates as inhibitors of the enzyme urease. Other prior art, as for example East German Pat. No. 149, 503 and U.S. Pat. Nos. 4,157,396, and 4,083,996 disclose the use of various hydroxamic acid derivatives as urease inhibitors. Great Britain Pat. No. 1,094,802 discloses that various maleimide derivatives can inhibit the activity of urease.

SUMMARY OF THE INVENTION

In accordance with the present invention, there is provided a unique fertilizer composition comprising urea or one or more compounds which are capable of forming urea in situ when subjected to the use conditions of the composition, and a "urease inhibiting effective amount" of one or more compounds of the formula:

A—R—B wherein:

A is a moiety of the formula:

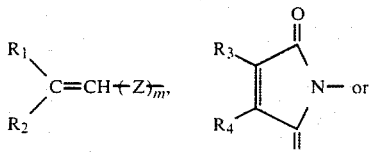

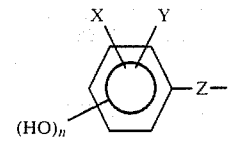

wherein:

$R_1$ and $R_2$ are the same or different and are individually halogen, trihalomethyl, cyano, alkylsulfonyl, arylsulfonyl, nitro, alkoxycarbonyl, arylcarbonyl, or alkylcarbonyl;

$R_3$ and $R_4$ are the same or different and are $R_1$, $R_2$ or hydrogen;

n is 1 or 2;

m is 0 or 1;

X and Y are the same or different and are hydrogen, alkyl, alkoxy, amino, nitro, isocyano, cyano, arylmercapto, isocyanato, mercapto, alkylmercapto, phenyl or phenoxy, or X and Y together may form a divalent alkylene or alkenylene chain completing a 5 or 6 membered aliphatic or aromatic ring structure;

B is moiety of the formula:

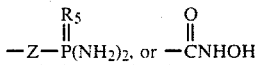

wherein:

$R_5$ is oxygen or sulfur;

Z is the same or different at each occurrence and is a divalent oxygen, nitrogen, sulfur, sulfinyl or sulfonyl group; and —R— is a divalent alkylene, arylene, cycloalkylene, alkenylene, cycloalkenylene, bicycloalkylene or bicycloalkenylene group, which group may optionally include one or more divalent carbonyl, oxygen, carbamyl, sulfur or nitrogen groups.

Hereinafter, the aforementioned compounds are referred to as "diaminophosphinyl or hydroxamic compounds".

Another aspect of this invention relates to a method of enhancing the yield of plants which comprises applying the composition of this invention to a plant growth medium within reach of the plant's root system, (hereinafter referred to as "root zone"). The term "plant growth medium" as herein employed refers to various natural and artificial medium which support plant growth, including soil, potting mixtures of organic and inorganic matter, and artificial medium such as polyurethane foams.

Yet another aspect of this invention relates to a composition comprising a "urease inhibiting effective amount" of one or more diaminophosphinyl or hydroxamic acid compounds, which composition is useful for carrying out the aforementioned method. As used herein "urease inhibiting effective amount" is an amount of one or more of the said diaminophosphinyl or hydroxamic acid compounds which when admixed with urea (or one or more urea precursor compounds capable of forming urea in situ under the use conditions of the composition); or when applied to a situs, as for example a plant growth medium is capable of inhibiting the catalytic activity of urease that may be in or at the medium or other situs to any extent.

It has been discovered by applying a urease inhibiting effective amount of one or more of the diaminophosphinyl or hydroxamic acid compounds to a plant growth medium or other situs the urease catalyzed hydrolysis of urea which may be present at the situs to ammonia is suppressed, thereby preventing the rapid loss of urea from the situs or medium. Furthermore, by proper distribution and/or application of the one or more diaminophosphinyl or hydroxamic acid compounds, this action of inhibiting the urease catalyzed hydrolysis of urea to ammonia is effective over a prolonged period of time.

DETAILED DESCRIPTION OF THE INVENTION

The application and/or distribution of a urease inhibiting effective amount of one or more of the above-identified diaminophosphinyl or hydroxamic acid compounds to a situs, such as a plant growth medium, or inclusion thereof in a composition and application and/or distribution of the composition to a situs is essential for the practice of this invention. While, the diaminophosphinyl or hydroxamic acid compounds can be used to inhibit the urease catalyzed hydrolysis of urea at any situs, they are especially useful for such inhibition in an agricultural context by application to a plant growth medium. In these preferred embodiments, usually, an acceptable level of urease inhibition can be achieved if at least about 0.01 parts by weight of said one or more diaminophosphinyl or hydroxamic acid compounds per one million parts by weight of soil or other plant growth medium. Hereinafter the abbreviation "p.p.m." is used to refer to parts by weight of one or more diaminophosphinyl or hydroxamic acid compounds per one million parts by weight of plant growth medium. In the preferred embodiments of this invention, the amount of said one or more diaminophosphinyl or hydroxamic acid compounds distributed in the said medium is from about 0.01 p.p.m. to about 5,000 p.p.m., and in the particularly preferred embodiments of the invention is from about 0.2 p.p.m. to about 1,000 p.p.m. Amongst these particularly preferred embodiments of the invention, most preferred are those embodiments of the invention in which the amount of said one or more diaminophosphinyl or hydroxamic acid compounds distributed in said medium is from about 1 p.p.m. to about 500 p.p.m.

Within the aforementioned limitations, the preferred amounts of the one or more diaminophosphinyl or hydroxamic acid compounds impregnated or distributed in the plant growth medium are dependent upon the particular situation. Thus, in determining the amount to be employed, consideration is made not only of the treatment need, i.e., soil pH, temperature, soil type, and the like, but also of the mode of application to the plant growth medium. When the one or more diaminophosphinyl or hydroxamic acid compounds are to be applied in a broadcast application, the amount in p.p.m. may frequently be less than in row or band application where, for a substantial depth and width within the vicinity of application, there can be a very high concentration of the one or more such compounds. When application is made near the root zone of growing plants, or when application is made immediately prior to seeding or transplanting, the amounts supplied are frequently at a lower rate than when application is made at the end of the growing season to prepare the plant growth medium for the following season. By dispersing very large dosages in the plant growth medium, a prolonged inhibition of urease activity can be obtained over a period of many months. The concentration of the one or more diaminophosphinyl or hydroxamic acid compounds is eventually reduced to a minimum by decomposition in the plant growth medium.

In one method for carrying out the present invention, one or more diaminophosphinyl or hydroxamic acid compounds are distributed throughout the plant growth medium in a broadcast application, such as by spraying, dusting, distributing in irrigation water and the like. In such application, the one or more diaminophosphinyl or hydroxamic acid compounds are supplied in amounts sufficient to permeate the growing area of the medium with a urease inhibiting effective amount of such diaminophosphinyl or hydroxamic acid compounds. In field administration, the one or more diaminophosphinyl or hydroxamic acid compounds can be distributed in the plant growth medium in an amount and through such cross-section of the medium as to provide for the presence therein of a urease inhibiting effective amount of the one or more diaminophosphinyl or hydroxamic acid compounds. It is usually preferred that the one or more diaminophosphinyl or hydroxamic acid compounds be distributed in the plant growth medium to a depth of at least two inches below the surface of the plant growth medium.

In another method for carrying out the present invention, one or more diaminophosphinyl or hydroxamic acid compounds are administered to the plant growth medium in a band or row application. In such application, administration is made with or without carrier in amounts sufficient to supply to the soil or other plant growth medium a urease inhibiting effective amount of the one or more diaminophosphinyl or hydroxamic acid compounds. After administration with or without discing or dragging, subsequent irrigation or rainfall distributes the one or more diaminophosphinyl or hydroxamic acid compounds throughout the plant growth medium.

In one embodiment of the present invention, the one or more diaminophosphinyl or hydroxamic acid compounds are distributed throughout the growth medium prior to seeding or transplanting the desired crop plant.

In another embodiment, the soil or plant growth medium within the root zone of growing plants is treated with the one or more diaminophosphinyl or hydroxamic acid compounds in an amount effective to inhibit the action of urease, but sublethal to plant growth. By following such practice, no adverse effect is exerted by the one or more diaminophosphinyl or hydroxamic acid compounds upon growth of seeds or plants. Oftentimes, it is desirable to treat the soil adjacent to plants, and this procedure may be carried out conveniently in side-dressing operations.

In a further embodiment of the invention, soil or other plant growth medium is treated with one or more diaminophosphinyl or hydroxamic acid compounds following harvest to prevent rapid loss of urea, and to prevent build-up of soil urease. Such practice conserves the soil nitrogen for the following growing season. In such application, the upper limit is primarily an economic consideration.

In an additional embodiment, the soil or plant growth medium can be impregnated with the one or more diaminophosphinyl or hydroxamic acid compounds in conjunction with the application of urea or one or more urea precursor compounds capable of forming urea in situ on application to the plant growth medium. Urea is a well known, commercially available compound and will not be discussed herein in detail. Illustrative of compounds which are believed to form urea on addition to the soil and are water soluble and formaldehyde condensation products, as for example methylolureas, methyleneureas and mixtures thereof. These products and a method for their preparation is described in detail in Justice U.S. Pat. No. 3,462,256. Still other useful sources of urea are water-insoluble urea formaldehyde condensation products such as ureaform. Illustrative of useful water-insoluble urea and formaldehyde condensation products are those whose preparation and use are described in detail in U.S. Pat. Nos. 3,677,736 and 4,033,745.

The present invention can be carried out by distributing one or more diaminophosphinyl or hydroxamic acid compounds in an unmodified form through a plant growth medium. The present method also embraces distributing one or more such compounds as a constituent in liquid or finely divided solid compositions.

The concentration of one or more diaminophosphinyl or hydroxamic acid compounds in compositions to be employed for the treatment of plant growth medium is not critical and can vary considerably provided the required dosage of the effective agents is supplied to the growth medium. In general, good results are obtained with liquid and/or solid compositions containing at least about 0.00001 percent by weight of the one or more diaminophosphinyl or hydroxamic acid compounds. Usually, however, the weight percent of the one or more diaminophosphinyl or hydroxamic acid compounds is from about 0.0001 percent to about 98 percent by weight on the same basis. In the preferred embodiments of the invention, the amount of the one or more diaminophosphinyl or hydroxamic acid compounds in the composition is from about 0.002 to about 50 weight percent, and in the particularly preferred embodiments is from about 0.01 to about 20 weight percent on the aforementioned basis. Liquid or dust compositions in which the one or more diaminophosphinyl or hydroxamic acid compounds is present in higher concentration can be utilized as such or can be employed as concentrate compositions to be diluted to prepare actual treating compositions.

In such practice, the one or more diaminophosphinyl or hydroxamic acid compounds can be modified with one or more additiments or soil treating adjuvants including water, petroleum distillates or other liquid carriers, surface-active dispersing agents, inert finely divided solids, an fertilizers, as for example urea, the aforementioned urea precursor compounds, and reduced nitrogen tertilizers such as ammonium nitrate and ammonia. These adjuvants cooperate with the one or more diaminophosphinyl or hydroxamic acid compounds so as to facilitate the practice of the present invention and to obtain an improved result. Preferred adjuvants are surface-active dispersing agents, inert finely divided solids and urea and/or urea precursor compounds. The amount of urea or urea precursor compound which may be included in the composition of this invention is not critical to the unique advantages thereof, and any amount known to those of skill in the art for use in fertilizers can be used. Normally, the amount employed will vary widely depending on a number of factors, including the times and frequency of application. In the preferred embodiments of the invention, the quantity of urea or urea precursor compound may vary from about 0.5 to about 95 weight percent based on the total weight of the composition and in the particularly preferred embodiments may vary from about 1 to about 50 weight percent on the same basis. In the most preferred embodiments of this invention, the quantity of urea or urea precursor compound will vary from about 3 to about 40 weight percent on the aforementioned basis.

The composition of this invention may include other optional ingredients known to those of skill in the art for inclusion in fertilizer compositions. For example, the composition may include sources of potassium, sulfur, phosphorus, boron, zinc, iron, manganese, copper, molybdenum, cobalt and like micronutrient and macronutrients which may be deficient in the soil. The composition may also include plant growth regulators, as for example auxins, cytokinins and the like, as well as pesticides, such as insecticides, miticides, herbicides, nematocides and the like. Moreover, the fertilizer composition can include sources of nitrogen other than urea, as for example ammonium nitrate and the like, and other materials which increase nitrogen efficiency, as for example, other urease inhibitors and nitrification inhibitors. Depending upon the concentration of the one or more diaminophosphinyl or hydroxamic acid compounds augmented compositions can be distributed in the plant growth medium without further modification or can be considered as concentrates and subsequently diluted with additional inert carrier to produce the ultimate treating composition.

Liquid compositions containing the desired amount of the one or more diaminophosphinyl or hydroxamic acid compounds can be prepared by dispersing the latter in one or more liquid carriers such as water or an organic solvent with or without the aid of a suitable surface active dispersing agent or emulsifying agent. Suitable organic solvents include acetone, diisobutylketone, methanol, ethanol, isopropyl alcohol, diethyl ether, toluene, methylene chloride, chlorobenzene and petroleum distillates. The preferred organic solvents are those which are of such volatility that they leave little permanent residue in the growth medium. Dispersing and emulsifying agents which can be employed in liquid compositions include condensation products of alkylene oxides with phenols and organic acids, alkyl aryl sulfonates, polyoxy-alkylene derivatives or sorbitol ester, sugar esters, complex ether alcohols, mahogany soaps and the like. The surface active agents are generally employed in the amount of from about 1 to about 20 percent by weight of the diaminophosphinyl or hydroxamic acid compounds and preferably in an amount of from about 1 to about 10 weight percent on the same basis.

Solid compositions containing the active one or more diaminophosphinyl or hydroxamic acid compounds can be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with a solid one or more diaminophosphinyl or hydroxamic acid compounds; or wet with a liquid one or more diaminophosphinyl or hydroxamic acid compounds; or wet with a solution or dispersion of a solid or liquid one or more diaminophosphinyl or hydroxamic acid compounds in a volatile organic solvent. Depending upon the proportions of ingredients, these compositions can be employed without further modification or be considered concentrates and subsequently further diluted with solid surface active dispersing agents, talc, chalk, gypsum, bentonite, diatomaceous earth, fullers earth, or the like to obtain the desired treating composition. Furthermore, such concentrate compositions can be dispersed in water with or without added dispersing agent or agents to prepare aqueous soil treating compositions.

The required amount of the one or more diaminophosphinyl or hydroxamic acid compounds contemplated herein may be applied per acre treated in from about 1 to about 200 gallons or more of liquid carrier and/or diluent or in from about 5 to about 500 pounds of inert solid carrier and/or diluent. The concentration in the liquid concentrate will usually vary from about 10 to about 95 percent by weight and in the solid formulations from about 0.5 to about 90 percent by weight. Satisfactory sprays, dusts, or granules for general use contain from about ¼ to about 15 pounds of active one or more diaminophosphinyl or hydroxamic acid compounds per acre.

The compounds contemplated herein prevent or retard the urease catalyzed hydrolysis of urea, and they have relatively high residual activity. With respect to plants they have a high margin of safety in that when used in sufficient amount to inhibit the activity of urease, they do not burn or injure the plant, and they resist weathering which includes wash-off caused by rain, decomposition by ultra-violet light, oxidation, or hydrolysis in the presence of moisture or, at least such decomposition, oxidation, and hydrolysis as would materially decrease the desirable urease inhibiting characteristic of the compounds or impart undesirable characteristics, for instance, phytotoxicity, to the compounds. The compounds are so chemically inert that they are compatible with substantially any other constituents of the spray schedule, and they may be used in the soil, upon the seeds, or the roots of plants without injuring either the seeds or roots of plants.

While the composition and method of this invention are particularly suited for agricultural applications for prevention or inhibition of urease catalyzed hydrolysis of urea, they can also be used in other applications where inhibition of the activity of urease is desired. For example, such other applications include use in animal litters, as feed additives, pharmaceutical applications, diaper treatment, urease inhibition in mammalian urinary tracts, and the like. It should be noted that while all of the above-identified compounds exhibit urease-inhibiting activity, the particular active compound employed in one application may not necessarily be useful in another application. Thus, in the selection of a particular active compound for use in an application, such factors are toxicity of the compound, the environment in which the compound will be used, level of urease inhibition desired and the like must be considered in selecting a particular compound for use.

Diaminophosphinyl or hydroxamic acid compounds which are useful as urease inhibitors in the composition of this invention are those of the formula:

A—R—B wherein:

"A" is a moiety of the formula:

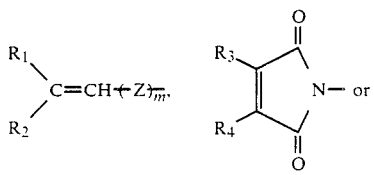

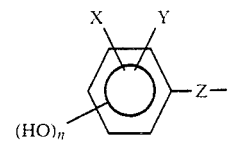

wherein:

n is 1 or 2;

m is 0 or 1;

$R_1$ and $R_2$ are the same or different and are trihalomethyl, cyano, alkylsulfonyl, arylsulfonyl, halogen, nitro, alkoxycarbonyl, arylcarbonyl, or alkylcarbonyl;

$R_3$ and $R_4$ are the same or different and are $R_1$, $R_2$ or hydrogen;

X and Y the same or different and are hydrogen alkyl, alkoxy, amino, nitro, isocyano, cyano, arylmercapto, isocyanato, mercapto, alkylmercapto, phenyl or phenoxy, or X or Y together may form an alkenylene or alkylene completing a 5 or 6 membered aliphatic or aromatic ring structure;

B is a moiety of the formula:

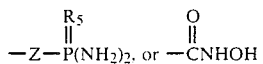

wherein:

$R_5$ is oxygen or sulfur;

Z is the same or different at each occurrence and is a divalent oxygen, nitrogen, sulfur, sulfinyl or sulfonyl group; and —R— is a divalent alkylene, arylene, cycloalkylene, alkenylene, bicycloalkylene, or bicycloalkenylene group, which group may optionally include one or more divalent carbonyl, oxygen, carbamyl, sulfur or nitrogen groups.

Illustrative of permissible $R_1$ and $R_2$ substituents are cyano, chloro, bromo, fluoro, nitro, methoxycarbonyl, trifluoromethyl, ethoxycarbonyl, acetyl, methylsulfonyl, phenylsulfonyl, benzoyl, hexanoyl, propanoyl and the like.

Examples of useful $R_3$ and $R_4$ substituents are bromo, chloro, nitro, hydrogen, cyano, acetyl, propoxycarbonyl, pentanoyl, and the like;

Exemplary of useful X and Y substituents are hydrogen, methyl, ethyl, propyl, methoxy, ethoxy, methylmercapto, ethylmercapto, amino, nitro and the like, or X and Y may form alkylene or alkenylene chains having from 1 to about 4 carbon atoms such as methylene, ethylene, propylene, butylene, propenylene, butenylene, and the like;

Useful $Z_1$ groups include divalent oxygen, divalent sulfur, divalent amino, and divalent alkylamino, such as methylamino, ethylamino, propylamino and the like, and useful R groups include divalent alkylene such as hexylene, octylene, dodecylene, methylene and butylene; divalent alkenylene such as propenylene, butenylene, hexenylene, octenylene, pentenylene and the like; arylenes such as phenylene, and decahydronaphthalene; and cycloalkylene, cyclopentylenes and bicycloalkylene such as cyclohexylene and bicyclo[2.2.2]octylene.

The following compounds are illustrative of diaminophosphinyl or hydroxamic acid compounds which can be employed in the practice of this invention.

N-(Diaminophosphinyl)-4-(1'-maleimido)butyramide
2-[1'-(3'-Chloro)maleimido]ethylphosphoric triamide
6-[1'-(3'-Bromo)maleimido]hexylphosphorodiamidate
N-(Diaminophosphinyl)-3-methyl-8-(1'-maleimido)octanamide
N-(Diaminophosphinyl)-3-[1'-(3'-chloro)maleimido]-2,2-dichloropropanamide
N-(Diaminophosphinyl)-5-[1'-(3',4'-dichloro)-maleimido]-3-cyanopentanamide
4-(1'-Maleimido)butylphosphoric triamide
6-[1'-(3'-Chloro)maleimido]-2,3-dibromohexyl phosphorodiamidate
9-[1'-(3',4'-Dichloro)maleimido]-5-nitrononyl phosphorodiamidate
7-[1'-(3'-Bromo)maleimido]-2,5-dimethylheptyl phosphorodiamidate
10-(1'-Maleimido)-3-chloro-5-cyano-7-fluorodecyl phosphorodiamidate
N-Methyl-N-[4-(3'-nitro-2'-propenyl)phenyl]phosphoric triamide
N-Ethyl-N-[3-(3'-cyano-2'-propenyl)phenyl]phosphoric triamide
2-[4-(3'-Nitro-2'-propenyl)phenylethylphosphorodiamidate
6-[4-(3'-Nitro-2'-propenyl)phenyl-2,3-dimethylhexyl phosphorodiamidate
5-(1'-Maleimido)pentylthiophosphoric triamide
8-[1'-(3'-Bromo)maleimido]octyl thiophosphorodiamidate
6-(3',4'-Dihydroxy-5'-chlorophenyl)hexyl thiophosphoro diamidate
10-(3'-Cyano-3'-carboethoxyallylamino)decylthiophosphoric triamide
4-(1'-Maleimido)butanehydroxamic acid
2-[1'-(3'-Chloro)maleimido]ethanehydroxamic acid
6-[1'-(3'-Bromo)maleimido]hexanehydroxamic acid
3-Methyl-8-(1'-maleimido)octanehydroxamic acid
3-[1'-(3'-Chloro)maleimido]-2,2-dichloropropane hydroxamic acid
5-[1'-(2',3'-Dichloro)maleimido]-3-cyanopentane hydroxamic acid
6-[1'-(3'-Chloro)maleimido]-2,3-dibromohexane hydroxamic acid
9-[1'-(3',4'-Dichloro)maleimido]-5-nitrononane hydroxamic acid
7-[1'-(3'-Bromo)maleimido]-2,5-dimethyl heptane hydroxamic acid
10-(1'-Maleimido)-3-chloro-5-cyano-7-fluorodecane hydroxamic acid
5-(1'-Maleimido)-3-pentenehydroxamic acid
4-(1'-Maleimido)benzohydroxamic acid
3-[1'-(3'-Chloro)maleimido]-5-methylbenzohydroxamic acid
4-[1'-(3',4'-Dichloro)maleimido]-2,5-dimethylbenzohydroxamic acid
5-(1'-Maleimido)naphthohydroxamic acid
4-[1'-(3'-Chloro)maleimido]-5-cyano-8-methylnaphthohydroxamic acid 4-[1'-(3',4'-Dichloro)maleimido]-2-furancarbohydroxamic acid
5-(1'-Maleimido)-3-pyridinecarbohydroxamic acid
4-[1'-(3'-Chloro)maleimido]-3-benzo[b]thiophene carbohydroxamic acid
4-[1'-(3'-Chloro)maleimido]cyclohexylphosphoric triamide
5-[1'-(3',4'-Dichloro)maleimido]bicyclo[3.2.1]octyl phosphoric triamide
6-(1'-Maleimido)bicyclo[2.2.1]hept-2-enyl phosphoric triamide
4-[1'-(3',4'-Dichloro)maleimido]cyclohexanehydroxamic acid
5-[1'-(3'-Chloro)maleimido]bicyclo[3.2.1]octane hydroxamic acid
6-(1'-Maleimido)bicyclo[2.2.1]hept-2-enehydroxamic acid
6-[3'-Cyano-3'-carbomethoxy allylamino]hexyl phosphoric triamide
5-[N-(2'-Nitro-2'-chlorovinyl)-N-methylamino]pentyl phosphoric triamide
N-Diaminophosphinyl-4-[5'-chloro-5'-cyano-4'-pentenyl]benzamide
4-[3'-cyano-3'-carboethoxyallylthio]butyl phosphorodiamidate
8-(3',4'-Dihydroxyphenyl)octylphosphoric triamide
4-[5'-Nitro-5'-carboethoxy-4'-pentenoylamino]benzohydroxamic acid
7-[N(2'-Nitro-2'-bromovinyl)-N-ethylamino]heptane hydroxamic acid
10-(3'-cyano-3'-carboethoxyallylthio)decanehydroxamic acid
6-(3',4'-Dihydroxyphenyl)hexylphosphorodiamidate
N-(Diaminophosphinyl)-4-(3',4'-dihydroxyphenyl)-butyramide
3-(5'-Chloro-5'-cyano-4'-pentenyl)benzohydroxamic acid
6-(3',4'-dihydroxy-6'-fluorophenyl)hexanehydroxamic acid
8-[5'-(2'',2''-Dicyanovinyl)-8'-cyano-naphthyl]octanehydroxamic acid
N-(Diaminophosphinyl)-10-(3',4'-dihydroxy-5'-methoxyphenyl)-2,2,3-trichlorodecanamide
6-(3',4'-Dihydroxyphenyl)cyclohexylphosphorodiamidate
N-(Diaminophosphinyl)-8-[5'-(3'',3''-dicyanoallyl)naphthyl]octanamide Preferred for use in the practice of this invention are compounds of the aforementioned generic formula in which:

A is a moiety of the formula:

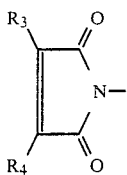

B is a moiety of the formula:

$$-\overset{O}{\underset{\|}{P}}(NH_2)_2 \quad \text{or} \quad \overset{S}{\underset{\|}{P}}(NH_2)$$

Amongst the preferred compounds, particularly preferred for use in this invention are compounds in which:

$R_3$ and $R_4$ are hydrogen, halogen, nitro or cyano;
$R_1$ is alkylene or alkenylene; and
B is diaminophosphinyl.

An especially effacious compounds for use in practice of this invention is N-(diaminophosphinyl)-4-(1'-maleimido)benzamide.

Compounds for use in the practice of this invention of the formula:

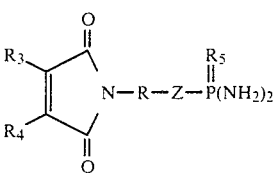

can be conveniently prepared in accordance with the following Reaction Scheme A:

Reaction Scheme A

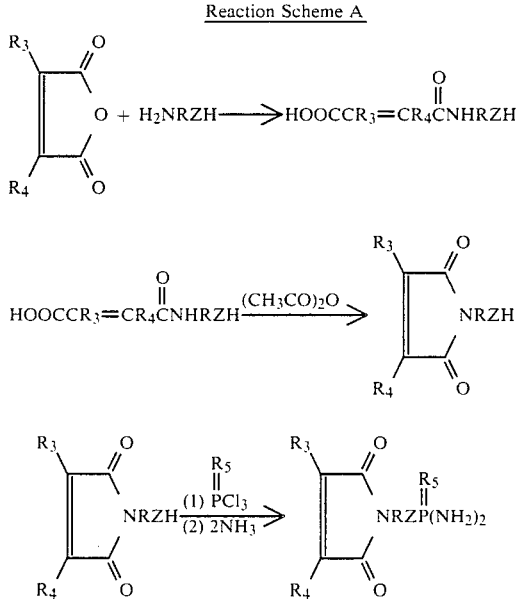

Compounds for use in the practice of this invention of the formula:

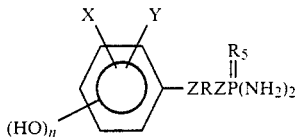

can be prepared in accordance with the following Reaction Scheme B:

Reaction Scheme B

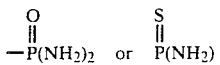

Compounds for use in this invention of the formula:

$$\underset{R_2}{\overset{R_1}{\diagdown}}C=CH{\left(Z\right)}_{\overline{m}}RZ\overset{R_5}{\underset{\|}{P}}(NH_2)_2$$

can be prepared in accordance with the following Reaction Scheme C:

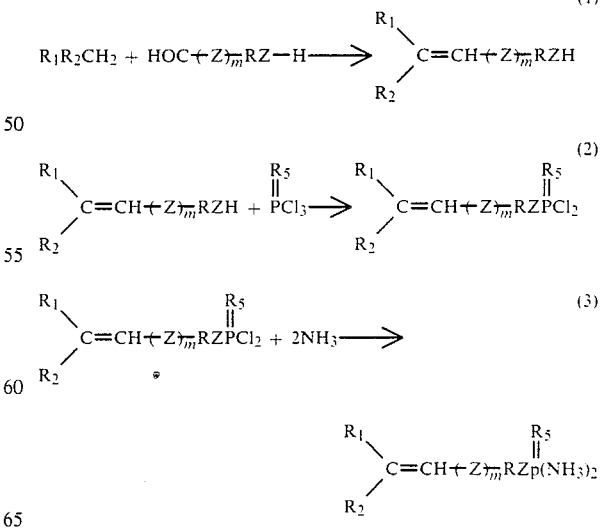

Compounds for use in this invention of the formula:

$$R_3 \overset{O}{\underset{R_4}{\diagdown}} \diagup N-R-\overset{O}{\overset{\|}{C}}NHOH$$
$$\underset{O}{\diagup}$$

can be prepared in accordance with the following Reaction Scheme D in which $R^1$ is alkyl:

Reaction Scheme D (1) $H_2N-R-COOR^1 + \underset{R_4}{\overset{R_3}{\diagdown}} \underset{O}{\diagup} \longrightarrow$ $HO\overset{O}{\overset{\|}{C}}-\underset{R_3}{\overset{}{C}}=\underset{R_4}{\overset{}{C}}-\overset{O}{\overset{\|}{C}}NHR\overset{O}{\overset{\|}{C}}OR^1$ (2) $HOOCR_3=CR_4\overset{O}{\overset{\|}{C}}NHRCOOR^1 \xrightarrow{(CH_3CO)_2O}$ $R_3 \overset{O}{\underset{R_4}{\diagdown}} \diagup NR\overset{O}{\overset{\|}{C}}OR^1$
$\underset{O}{\diagup}$ (3) $R_3 \overset{O}{\underset{R_4}{\diagdown}} \diagup N-R-\overset{O}{\overset{\|}{C}}OR^1 \xrightarrow{NH_2OH}$ $R_3 \overset{O}{\underset{R_4}{\diagdown}} \diagup N-R-\overset{O}{\overset{\|}{C}}NHOH$
$\underset{O}{\diagup}$ Compounds for use in the practice of this invention of the formula:

[phenyl ring with X, Y, $(HO)_n$ substituents]—Z—R—CONHOH can be prepared in accordance with the following Reaction Scheme E in which $R^1$ is alkyl:

Reaction Scheme E (1) [phenyl ring with X, Y, $(HO)_n$]—ZR¹ $\xrightarrow{NaCN}$ [phenyl ring with X, Y, $(HO)_n$]—ZRCN (2) [phenyl ring]—ZRCN $\xrightarrow[H^+]{R^1OH}$

[phenyl ring with X, Y, $(HO)_n$]—ZR$\overset{O}{\overset{\|}{C}}$OR¹

(3) [phenyl ring]—ZR$\overset{O}{\overset{\|}{C}}$OR¹ $\xrightarrow{NH_2OH}$

[phenyl ring with X, Y, $(HO)_n$]—ZR$\overset{O}{\overset{\|}{C}}$NHOH

Compounds for use in the practice of this invention of the formula:

$\underset{R_2}{\overset{R_1}{\diagdown}}C=CH(Z)_m-R-\overset{O}{\overset{\|}{C}}NHOH$ can be prepared in accordance with the following Reaction Scheme F:

Reaction Scheme F (1) $\underset{R_2}{\overset{R_1}{\diagdown}}CH_2 + HOC(Z)_{\overline{m}}RCOOCH_3 \longrightarrow$ $R_1R_2C=CH(Z)_{\overline{m}}RCOOCH_3$ (2) $R_1R_2C=CH(Z)_{\overline{m}}RCOOCH_3 + NH_2OH \longrightarrow$ $R_1R_2C=CH(Z)_{\overline{m}}RCONHOH$ Briefly stated, in each step of the above reaction schemes substantially equal molar amounts or excesses of the reactants are contacted neat or in an inert solvent. Useful inert reaction solvents include ethyl ether, carbon tetrachloride, methylene chloride, benzene, dioxane, toluene, xylene, tetrahydrofuran, methyl sulfoxide, dimethylformamide and the like.

Reaction temperatures and pressures are not critical. The reaction can be conveniently carried out at a temperature of from about −20° C. to about 100° C., but is preferably carried out at a temperature of from about 25° C. to about 75° C. The reaction can be carried out at atmospheric, sub-atmospheric or super-atmospheric pressure. For convenience, however, the reaction is carried out at atmospheric or autogeneous pressure.

The order in which the reactants are reacted indicated in the reaction scheme is for illustrative purposes only, and the order of the reactions is not critical. The exact proportions of the reactants are not critical, some of the desired product being obtained when the reactants are employed in any proportions.

Reaction times are not critical and can be varied widely depending on such factors as the reaction temperature, reactivity of the reactants, and the like. The reaction mixture is usually held within the desired reaction temperature range for a period of time, conveniently from about 1 to about 24 hours before cooling. Good yields are obtained with reaction times of from 2 to about 5 hours.

After the reactions have gone substantially to completion, the phosphorodiamide product can be separated by such conventional procedures as evaporation, and purified by conventional procedures such as distillation and extraction. The product separated as described above can be employed in the control of urease in the soil or in other applications in accordance with this invention or may be further purified by conventional procedures such as extraction and distillation.

The following specific examples are presented to more particularly illustrate the invention.

EXAMPLE I

Preparation of
N-(Diaminophosphinyl)-4-(1'-maleinmido)benzamide

Step A

A solution of p-aminobenzamide (8.64 g, 40 mmol) in dimethylformamide (100 mL) was added dropwise to a vigorously stirred solution of maleic anhydride (3.96 g, 40 mmol) in anhydrous ether (200 mL). Stirring was continued at room temperature for 90 minutes, after which the solid product was separated by filtration, rinsed with ether-DMF (10:1) and ether, and dried. The yield of p-maleimidobenzamide was 11.35 g (90%). The product was purified by crystallization from ethanol, mp 104° to 106° C.

Ir (KBr): 3430, 3325, 1630, 1610, 1525, 1405 cm$^{-1}$;

$^1$H NMR (DMSO-d$_6$): δ8.2–7.6 (m, 4H, aromatic) 6.6 ppm (d of d, 2H, CH=). The pattern of the NMR spectrum in the region of 5.0–9.0 ppm resembles closely the spectrum of 4'-carboxymaleanilic acid 4'-ethylester in the Sadtler Catalog of Infrared Spectra, No. 14,579.

Step B

The product from the Step A (4'-amide of 4'-carboxymaleanilic acid, (3.18 g, 13.6 mmol) was mixed with anhydrous sodium acetate (0.4 g), acetic anhydride (4.0 mL), and dimethylformamide (10 mL). The reaction mixture was stirred and heated rapidly (within 5 minutes) to a temperature of 80° C. and maintained at a temperature of 80° C.-100° C. for the next 10 minutes. The reaction mixture was then poured into ice-cold water (120 mL). The precipitated solid was collected by filtration, washed with water, alcohol, and ether, and dried in vacuum. The yield was 2.0 g (68%).

$^1$H NMR (DMSO-d$_6$): δ8.10–7.15 (m, 4H, aromatic) and 7.08 ppm (s, 2H, =CH). The $^1$H NMR spectrum in the region δ8.5–6.0 ppm resembles closely the spectrum of the ethyl ester of p-maleimido benzoic acid (see Sadtler Catalog of Infrared Spectra, No. 14580).

Steps C and D p-Maleimidobenzamide (2.16 g, 10 mmol) and phosphorus pentachloride (2.08 g, 10 mmol) were added to carbon tetrachloride (40 mL). The resulting mixture was stirred and heated under nitrogen for 45 minutes, with evolution of gas and then refluxed for 30 minutes. The reaction mixture was cooled to room temperature, filtered and the filtrate treated with formic acid (0.4 mL, 10 mmol). The resulting precipitate was separated by filtration, rinsed with carbon tetrachloride and ether, and dried in vacuum over phosphorus pentoxide at room temperature. The yield was 2.0 g (60%).

IR (KBr): 1720, 1435, 1380, 1240, 840 cm$^{-1}$;

$^1$H NMR (DMSO-d$_6$): δ8.4–7.15 (m, 4H, aromatic) and 7.1 ppm (s, 2H, =CH).

Step E:

The intermediate compound prepared in the previous step (1.45 g, 4.9 mmol) was added to a saturated solution of ammonia in ether (400 mL) at 0° C. under nitrogen. The reaction mixture was stirred and allowed to return to room temperature over a 2 hour period. The solid was separated by filtration, rinsed, dried, and crystallized from water.

IR (KBr): 3260, 1630, 1593, 1540, 1430, 1270, 1210, 885, 850 cm$^{-1}$;

$^1$H NMR: δ8.1–7.3 (m, 4H, aromatic), 6.35

(s, 2H, =CH), and 4.17 ppm (br s, 4H, NH$_2$).

EXAMPLE II

Efficacy tests were conducted with jack bean urease. The procedure of Bremner (See. L. A. Douglas, J. M. Bremner, *Soil Biology Biochem.*, 3, 859–859 (1970), and references cited therein was modified by replacing the soil as the source of urease with commercial purified jack bean urease. The incubation then proceeds in aqueous solution. The results are set forth in the following Table I.

TABLE I

| | Urease Inhibition in Solution | | |
|---|---|---|---|
| | | % Inhibition at Specific Concentration | |
| Exp. No. | Compound | 10$^{-6}$ M | 10$^{-7}$ M |
| 1. | N—(Diaminophosphinyl)-4-(1'-maleimido)benzamide | 59 | 8 |

What is claimed is:

1. A urease inhibiting composition comprising an acceptable carrier and a urease inhibiting effective amount of one or more compounds of the formula:

A—R—B wherein:

"A" is a moiety of the formula:

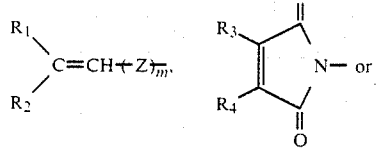 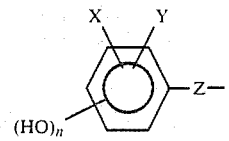

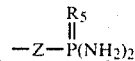

wherein:
n is 1 or 2;
m is 0 or 1;
R₁ and R₂ are the same and different and are trihalomethyl, cyano, alkylsulfonyl, arylsulfonyl, halogen, nitro, alkoxycarbonyl, arylcarbonyl, or alkylcarbonyl;
R₃ and R₄ are the same are different and are R₁, R₂ or hydrogen;
X and Y are the same or different and are hydrogen, alkyl, alkoxy, amino, nitro, isocyano, cyano, isocyanato, mercapto, alkylmercapto, phenyl or phenoxy, or X and Y together may form an alkylene or a alkenylene chain completing a 3, 4, 5 or 6 membered aliphatic or aromatic ring structure; and
B is a moiety of the formula:

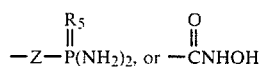

wherein:
R₅ is oxygen or sulfur;
Z is the same or different at each occurrence and is a divalent oxygen, sulfur, nitrogen, sulfinyl or sulfonyl group; and
R is alkylene, alkenylene, cycloalkylene, arylene, cycloalkenylene, bicycloalkylene, or bicycloalkenylene groups, which groups may optionally include one or more divalent carbonyl, oxygen, sulfur or nitrogen groups.

2. A composition according to claim 1 wherein said urease inhibiting amounts is at least about 0.00001 weight percent based on the total weight of the composition.

3. A composition according to claim 2 wherein said amount is from about 0.00001 to about 98 weight percent.

4. A composition according to claim 3 wherein said amount is from about 0.002 to about 50 weight percent.

5. A composition according to claim 4 wherein said amount is from about 0.01 to about 20 weight percent.

6. A composition according to claim 1 wherein A is a moiety of the formula:

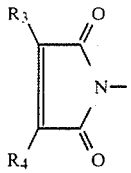

7. A composition according to claim 6 wherein R₃ and R₄ are the same or different and are hydrogen, halogen, nitro or cyano.

8. A composition according to claim 7 wherein R₃ and R₄ are the same.

9. A composition according to claim 8 wherein R₃ and R₄ are hydrogen.

10. A composition according to claim 9 wherein B is a moiety of the formula:

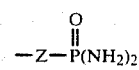

11. A composition according to claim 10 wherein B is a moiety of the formula:

12. A composition according to claim 1 wherein —R— is divalent alkylene, arylene of alkenylene.

13. A composition according to claim 12 wherein —R— is alkylene.

14. A composition according to claim 12 wherein —R— is arylene which includes one divalent carbonyl function.

15. A composition according to claim 1 wherein said compound is N-(diaminophosphinyl)-4-(1'-maleimido)-benzamide.

16. A method of inhibiting the urease catalyzed hyrolysis of urea at a situs which comprises applying to said situs a urease inhibiting effective amount of one or more compounds of the formula:

A—R—B wherein:
"A" is a moiety of the formula:

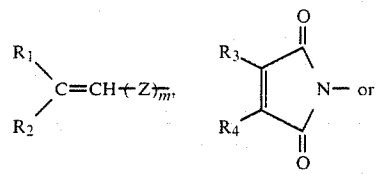

wherein:
n is 1 or 2;
m is 0 or 1;
R₁ and R₂ are the same and different and are trihalomethyl, cyano, alkylsulfonyl, arylsulfonyl halogen, nitro, alkoxycarbonyl, arylcarbonyl or alkylcarbonyl;
R₃ and R₄ are the same are different and are R₁, R₂ or hydrogen;
X and Y are the same or different and are hydrogen, alkyl, alkoxy, amino, nitro, isocyano, cyano, isocyanato, mercapto, alkylmercapto, phenyl or phenoxy, or X and Y together may form an alkylene or a alkenylene chain completing a 5 or 6 membered aliphatic or aromatic ring structure;

B is a moiety of the formula:

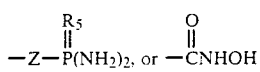

wherein:

$R_5$ is oxygen or sulfur;

Z is the same or different at each occurrence and is a divalent oxygen, sulfur, nitrogen, sulfinyl or sulfonyl groups; and —R— is alkylene, alkenylene, cycloalkylene, arylene, cycloalkenylene, bicycloalkylene, or bicycloalkenylene groups, which groups may optionally include one or more divalent carbonyl, oxygen, sulfur or nitrogen groups.

17. A method according to claim 16 wherein said situs is a plant growth medium.

18. A method according to claim 17 wherein said one or more compounds are applied to said medium prior to or in conjunction with the applicatin of urea or one or more compounds capable of forming urea in situ to said medium.

19. A method according to claim 16 wherein said urease inhibiting effective amount is at least about 0.01 p.p.m.

20. A method according to claim 19 wherein said amount is from about 0.01 p.p.m. to about 5,000 p.p.m.

21. A method according to claim 20 wherein said amount is from about 0.2 p.p.m. to about 1000 p.p.m.

22. A method according to claim 21 wherein said amount is from about 1 p.p.m. to about 500 p.p.m.

23. An improved fertilizer composition which comprises urea and/or one or more urea precursor compounds capable of forming urea in situ when subjected to the use conditions of the composition, and a urease inhibiting effective amount of one or more compounds of the formula:

wherein:

"A" is a moiety of the formula:

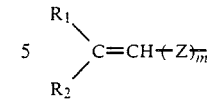

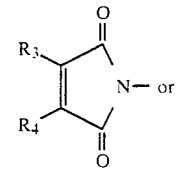

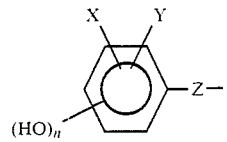

wherein:

n is 1 or 2;

m is 0 or 1;

$R_1$ and $R_2$ are the same and different and are trihalomethyl, cyano, alkylsulfonyl, arylsulfonyl halogen, nitro, alkoxycarbonyl, arylcarbonyl, alkylcarbonyl;

$R_3$ and $R_4$ are the same are different and are $R_1$, $R_2$ or hydrogen;

X and Y are the same or different and are hydrogen, alkyl, alkoxy, amino, nitro, isocyano, cyano, isocyanato, mercapto, alkylmercapto, phenyl, or phenoxy, X and Y together may form an alkylene or alkenylene chain completing a 5 or 6 membered aliphatic or aromatic ring structure;

B is a moiety of the formula:

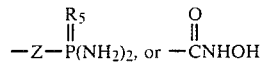

wherein:

Z is the same or different at each occurrence and is a divalent oxygen, sulfur, nitrogen, sulfinyl or sulfonyl group; and R is alkylene, alkenylene, cycloalkylene, arylene, cycloalkenylene, bicycloalkylene, or bicycloalkenylene groups, which groups may optionally include one or more divalent carbonyl, oxygen, sulfur or nitrogen groups.

24. A method of enhancing plant growth and crop yield which comprises applying an effective amount of the composition according to claim 23 to the plant growth medium surrounding the plant.

25. A composition according to claim 1 wherein said carrier is a liquid.

26. A composition according to claim 25 wherein said liquid carrier is selected from the group consisting of water and organic liquids.

27. A composition according to claim 1 wherein said carrier is finely divided inert solid.

* * * * *